(12) United States Patent
Fukuzawa et al.

(10) Patent No.: US 11,529,631 B2
(45) Date of Patent: Dec. 20, 2022

(54) REACTION PROCESSOR

(71) Applicant: Nippon Sheet Glass Company, Limited, Tokyo (JP)

(72) Inventors: Takashi Fukuzawa, Tokyo (JP); Osamu Kawaguchi, Kanagawa (JP)

(73) Assignee: Nippon Sheet Glass Company, Limited, Tokyo (JP)

( * ) Notice: Subject to any disclaimer, the term of this patent is extended or adjusted under 35 U.S.C. 154(b) by 117 days.

(21) Appl. No.: 16/723,150

(22) Filed: Dec. 20, 2019

(65) Prior Publication Data

US 2020/0139371 A1 May 7, 2020

Related U.S. Application Data

(63) Continuation of application No. PCT/JP2018/023073, filed on Jun. 18, 2018.

(30) Foreign Application Priority Data

Jun. 23, 2017 (JP) .............................. JP2017-123604

(51) Int. Cl.
    *B01L 3/00*     (2006.01)
    *B01L 7/00*     (2006.01)

(52) U.S. Cl.
    CPC ..... *B01L 3/502769* (2013.01); *B01L 3/50273* (2013.01); *B01L 3/502723* (2013.01);
(Continued)

(58) Field of Classification Search
None
See application file for complete search history.

(56) References Cited

U.S. PATENT DOCUMENTS

2010/0167384 A1* 7/2010 Clemmens ............. C12M 25/16
    435/286.7

FOREIGN PATENT DOCUMENTS

EP     0637999 A1 *   2/1995   ............ B01L 3/5027
EP     0637999 A1     2/1995
(Continued)

OTHER PUBLICATIONS

International Search Report for PCT/JP2018/023073 dated Sep. 11, 2018.
(Continued)

*Primary Examiner* — Matthew D Krcha
(74) *Attorney, Agent, or Firm* — Sughrue Mion, PLLC

(57) ABSTRACT

A reaction processor includes: a reaction processing vessel including a channel in which a sample moves and a pair of air communication ports, a first air communication port and a second air communication port, provided at respective ends of the channel; a temperature control system that provides a medium temperature region and a high temperature region between the first air communication port and the second air communication port in the channel; and a liquid feeding system that discharges and sucks air in order to move and stop the sample inside the channel. One of the pair of air communication ports of the reaction processing vessel that is farther away from the high temperature region communicates with the liquid feeding system via a tube. One of the pair of air communication ports of the reaction processing vessel that is closer to the high temperature region is opened to atmospheric pressure.

4 Claims, 11 Drawing Sheets

Specification includes a Sequence Listing.

(52) U.S. Cl.
CPC ........... *B01L 7/52* (2013.01); *B01L 2300/048* (2013.01); *B01L 2300/0681* (2013.01); *B01L 2300/0816* (2013.01); *B01L 2300/0883* (2013.01); *B01L 2300/18* (2013.01); *B01L 2400/0475* (2013.01)

(56) References Cited

FOREIGN PATENT DOCUMENTS

| | | |
|---|---|---|
| JP | 7-506258 A | 7/1995 |
| JP | 2009-232700 A | 10/2009 |
| WO | 2017094674 A1 | 6/2017 |
| WO | 2018/084017 A1 | 5/2018 |
| WO | 2018/105404 A1 | 6/2018 |

OTHER PUBLICATIONS

International Preliminary Report on Patentability with Written Opinion of the International Searching Authority for PCT/JP2018/023073 dated Jan. 2, 2020.
Communication dated Feb. 12, 2021, issued by the European Patent Office in counterpart European Application No. 18819591.1.
Office Action dated Feb. 22, 2022 in Japanese Application No. 2019-525601.

* cited by examiner

| SPECIMEN CONCENTRATION (Copies/μL) | SPECIMEN CONCENTRATION (LOGARITHM (BASE 10)) | Ct値 |
|---|---|---|
| 1×10¹ | 1 | 45.91 |
| 1×10² | 2 | 42.07 |
| 1×10³ | 3 | 38.95 |
| 1×10⁴ | 4 | 34.79 |
| 1×10⁵ | 5 | 31.18 |
| 1×10⁶ | 6 | 28.43 |

```
                          SEQUENCE LISTING

<160> NUMBER OF SEQ ID NOS: 3

<210> SEQ ID NO 1
    <211> LENGTH: 22
    <212> TYPE: DNA
    <213> ORGANISM: Artificial Sequence
    <220> FEATURE:
    <223> OTHER INFORMATION: Forward PCR Primer

<400> SEQUENCE: 1
gtgtgatatc tacccgcttc gc                                          22

<210> SEQ ID NO 2
    <211> LENGTH: 24
    <212> TYPE: DNA
    <213> ORGANISM: Artificial Sequence
    <220> FEATURE:
    <223> OTHER INFORMATION: Reverse PCR Primer

<400> SEQUENCE: 2
agaacggttt gtggttaatc agga                                        24

<210> SEQ ID NO 3
    <211> LENGTH: 22
    <212> TYPE: DNA
    <213> ORGANISM: Artificial Sequence
    <220> FEATURE:
    <223> OTHER INFORMATION: TaqMan(R) Probe

<400> SEQUENCE: 3
tcggcatccg gtcagtggca gt                                          22
```

REACTION PROCESSOR

BACKGROUND OF THE INVENTION

1. Field of the Invention

The present invention relates to reaction processors used for polymerase chain reactions (PCR).

BACKGROUND ART

Genetic testing is widely used for examinations in a wide variety of medical fields, identification of farm products and pathogenic microorganisms, safety assessment for food products, and even for examinations for pathogenic viruses and a variety of infectious diseases. In order to detect with high sensitivity a minute amount of DNA, methods of analyzing the resultant obtained by amplifying a portion of DNA are known. Above all, a method that uses PCR is a remarkable technology where a certain portion of a very small amount of DNA collected from an organism or the like is selectively amplified.

In PCR, a predetermined thermal cycle is applied to a sample in which a biological sample containing DNA and a PCR reagent consisting of primers, enzymes, and the like are mixed so as to cause denaturation, annealing, and elongation reactions to be repeated so that a specific portion of DNA is selectively amplified.

It is a common practice to perform PCR by putting a predetermined amount of a target sample into a PCR tube or a reaction processing vessel such as a microplate (microwell) in which a plurality of holes are formed. However, in recent years, PCR using a reaction processing vessel (also referred to as "chip") provided with a micro-channel that is formed on a substrate is practiced (e.g. Patent Document 1).

[Patent Document 1] JP 2009-232700

SUMMARY OF THE INVENTION

While PCR allows for the replication of millions of DNA molecules, PCR is very sensitive to contaminants. Thus, when starting a reaction using a very small amount of sample DNA, contamination from a product of a previous reaction becomes an issue. A phenomenon in which the product of a previous reaction affects the subsequent reaction is called "carryover". The prevention and reduction of carryover is very important. This is because, for example, a previous reaction product containing a target sequence may result in misinterpretation in a result even when only one copy is involved in the contamination in a reaction system.

In this background, a purpose of the present invention is to provide a reaction processor capable of preventing or at least suppressing carryover in PCR.

Means to Solve the Problem

A reaction processor according to one embodiment of the present invention includes: a reaction processing vessel including a channel in which a sample moves and a pair of air communication ports provided at respective ends of the channel; a temperature control system that provides a first temperature region maintained at a first temperature and a second temperature region maintained at a second temperature higher than the first temperature between the pair of air communication port in the channel; and a liquid feeding system that discharges and sucks air in order to move and stop the sample inside the channel. One of the pair of air communication ports of the reaction processing vessel that is farther away from the second temperature region communicates with the liquid feeding system via a tube, and one of the pair of air communication ports of the reaction processing vessel that is closer to the second temperature region is opened to atmospheric pressure.

The liquid feeding system may include: a chamber that has an internal space having a constant volume and a first air vent and a second air vent that allow the internal space to communicate with the outside; a first pump that is arranged so as to discharge air to the internal space of the chamber from the first air vent; and a second pump that is arranged so as to discharge air to the internal space of the chamber from the second air vent. The first air vent of the chamber may communicate with one of the pair of air communication ports of the reaction processing vessel that is farther away from the second temperature region via the tube, the second air vent of the chamber may be opened to atmospheric pressure, and the first pump and the second pump may be controlled so as to alternately perform air discharging operation.

A filter may be provided at least at one of the ends of the channel of the reaction processing vessel that is farther away from the second temperature region.

BRIEF DESCRIPTION OF THE DRAWINGS

Embodiments will now be described, byway of example only, with reference to the accompanying drawings which are meant to be exemplary, not limiting, and wherein like elements are numbered alike in several Figures, in which.

DETAILED DESCRIPTION OF THE INVENTION

Figure 1A:
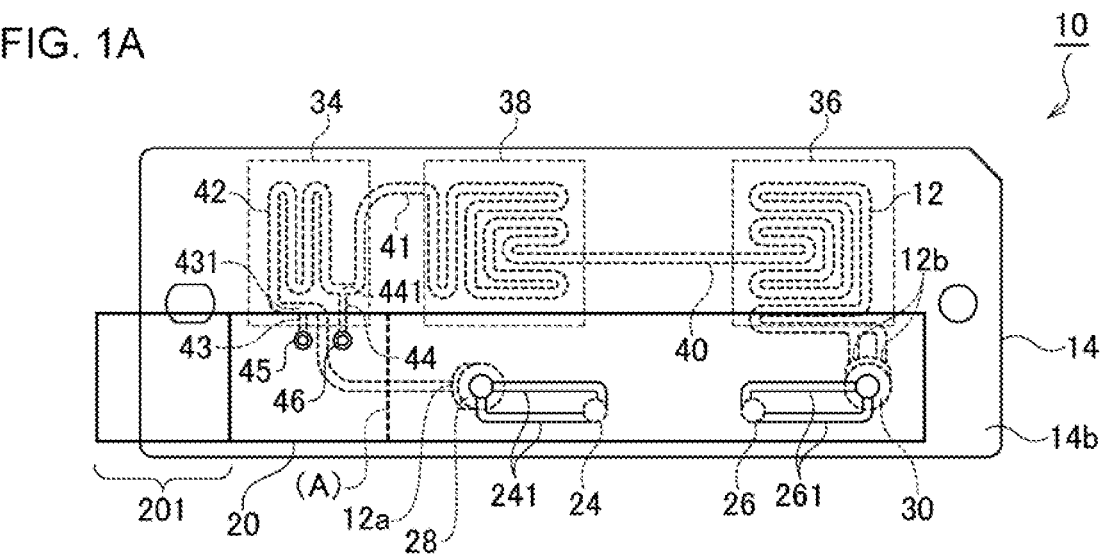
FIGS. 1A, 1B, and 1C are diagrams for explaining a reaction processing vessel usable in a reaction processor according to an embodiment of the present invention.

An explanation will be given in the following regarding a reaction processor according to an embodiment of the present invention. The same or equivalent constituting elements, members, and processes illustrated in each drawing shall be denoted by the same reference numerals, and duplicative explanations will be omitted appropriately. Further, the embodiments do not limit the invention and are shown for illustrative purposes, and all the features described in the embodiments and combinations thereof are not necessarily essential to the invention.

Figure 1B:
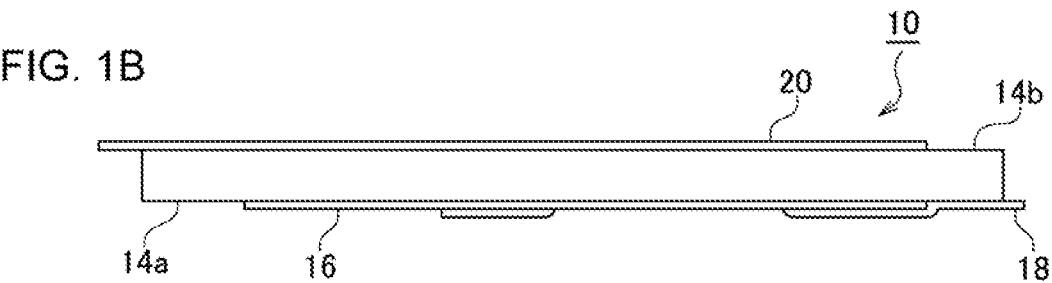
Figure 1C:
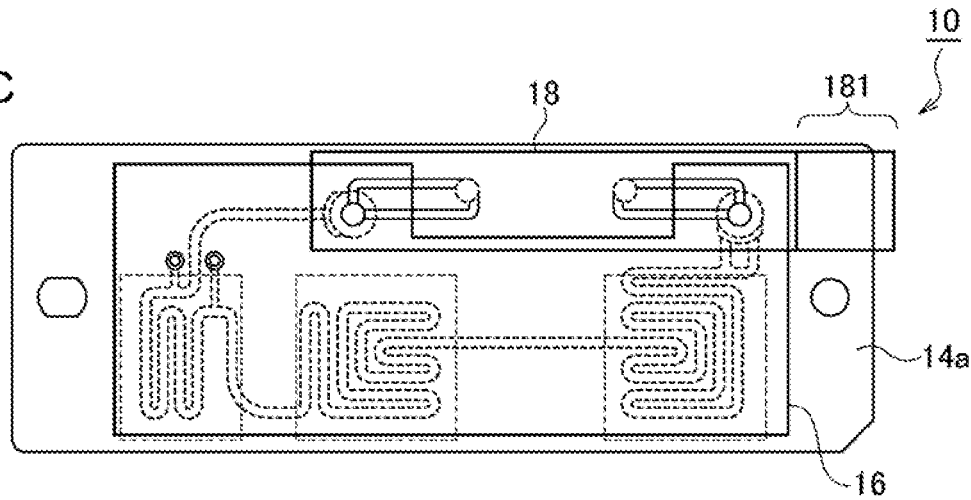
Figure 2:
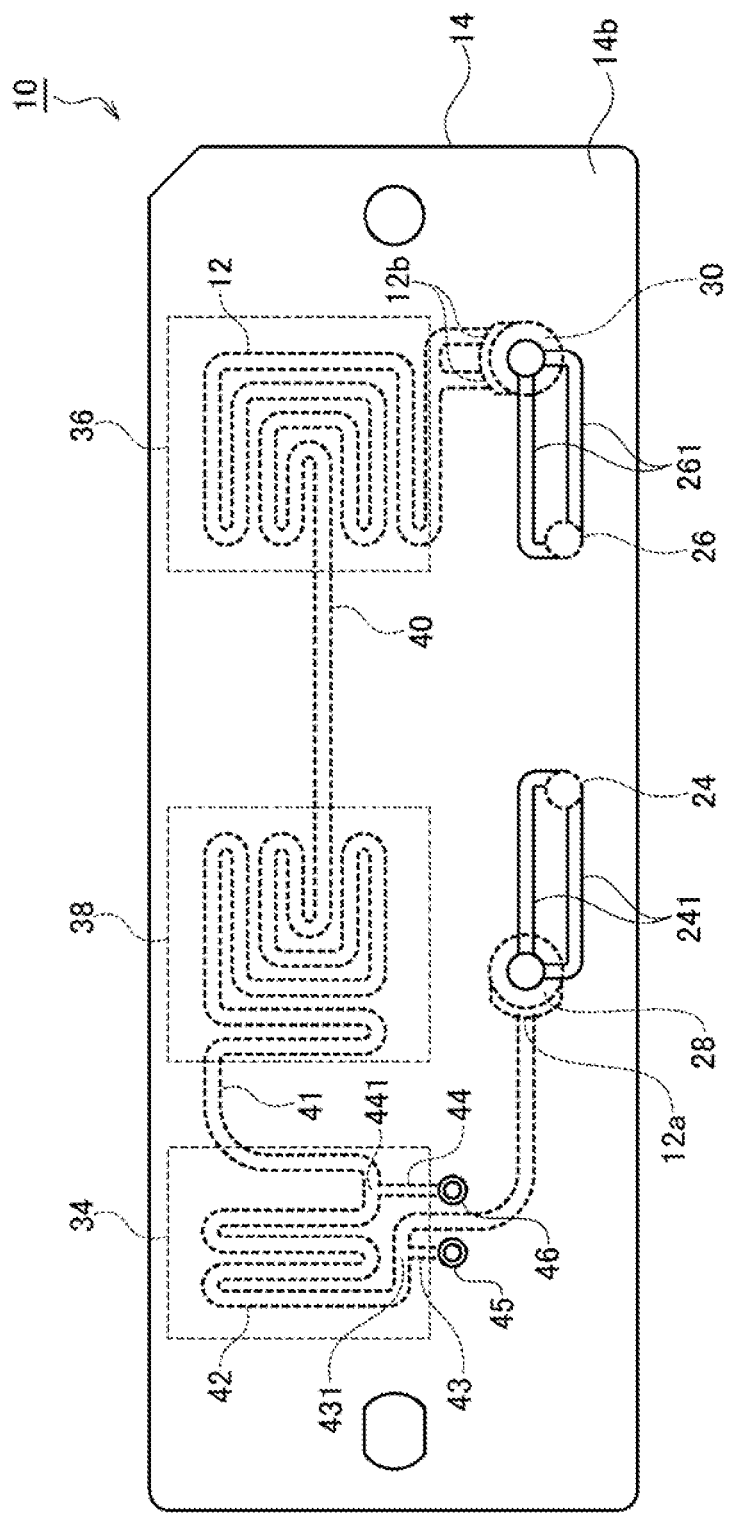
FIG. 2 is a plan view of a substrate provided in the reaction processing vessel.

FIGS. 1A, 1B, and 1C are diagrams for explaining a reaction processing vessel 10 usable in a reaction processor according to an embodiment of the present invention. FIG. 1A is a plan view of the reaction processing vessel 10, FIG. 1B is a front view of the reaction processing vessel 10, and FIG. 1C is a bottom view of the reaction processing vessel 10. FIG. 2 is a plan view of a substrate 14 provided in the reaction processing vessel 10.

Figure 3:
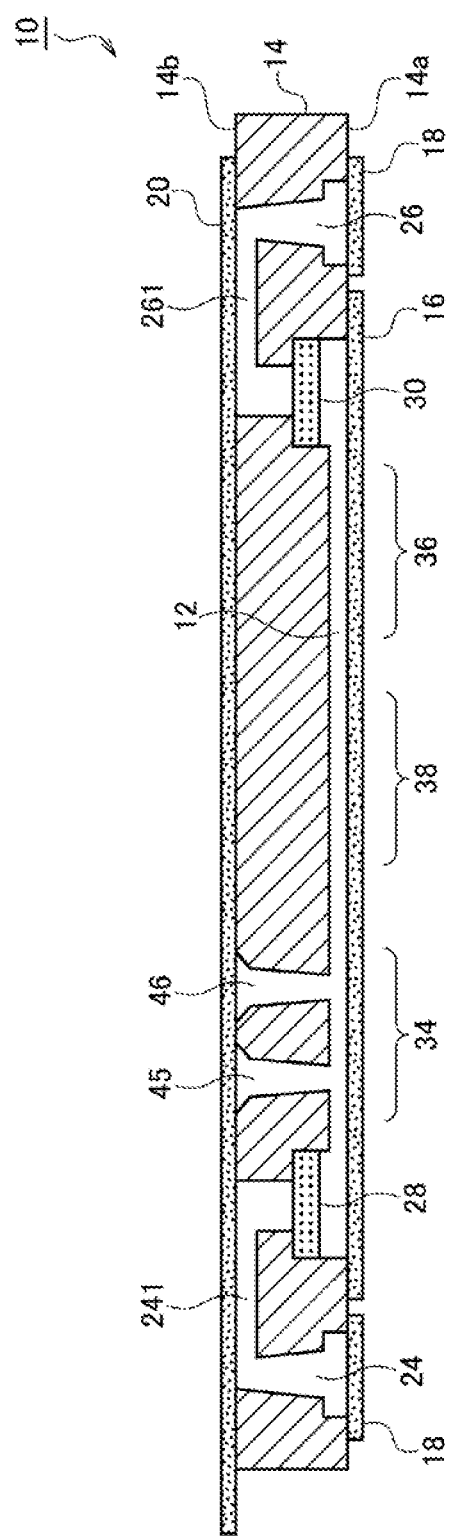
FIG. 3 is a cross-sectional view of the reaction processing vessel and is a diagram for explaining the relationship between each part and the principal surface of the substrate.

FIG. 3 is a conceptual cross-sectional view for explaining the reaction processing vessel 10. The reaction processing vessel 10 comprises a resinous substrate 14 having a groove-like channel 12 formed on a lower surface 14a thereof, a channel sealing film 16 for sealing the channel 12, which is attached on the lower surface 14a of the substrate 14, and a first sealing film 18 for sealing a first air communication port 24 and a second air communication port 26, which is also attached on the lower surface 14a of the substrate 14, and a second sealing film 20 for sealing a first sample introduction port 45 and a second sample introduction port 46, which is attached on an upper surface 14b of the substrate 14. FIG. 3 is a diagram for explaining how these are arranged with respect to the substrate 14.

The substrate 14 is preferably formed of a material that is stable under temperature changes and is resistant to a sample solution that is used. Further, the substrate 14 is preferably formed of a material that has good moldability, a good transparency and barrier property, and a low self-fluorescent property. As such a material, an inorganic material such as glass, silicon (Si), or the like, a resin such as acrylic, polypropylene, silicone, or the like, and particularly a cycloolefin polymer resin (COP) are preferred. An example of the dimensions of the substrate 14 includes a long side of 76 mm, a short side of 26 mm, and a thickness of 3 mm.

The groove-like channel 12 is formed on the lower surface 14a of the substrate 14. In the reaction processing vessel 10, most of the channel 12 is formed in the shape of a groove exposed on the lower surface 14a of the substrate 14. This is for allowing for easy molding by injection molding using a metal mold or the like. In order to seal this groove so as to make use of the groove as a channel, the channel sealing film 16 is attached on the lower surface 14a of the substrate 14. The cross-sectional shape of the groove is not particularly limited and may be rectangular or U-shaped (round shaped). Further, the shape may be a shape narrowed in a tapered manner from the lower surface 14a in the depth direction in order to improve the mold release property at the time of molding and may be, for example, a trapezoid shape. An example of the dimensions of the channel 12 includes a width of 0.7 mm and a depth of 0.7 mm at most.

The channel sealing film 16 may be sticky on one of the principal surfaces thereof or may have a functional layer that exhibits stickiness or adhesiveness through pressing, energy irradiation with ultraviolet rays or the like, heating, etc., formed on one of the principal surfaces. Thus, the channel sealing film 16 has a function of being easily able to become integral with the lower surface 14a of the substrate 14 while being in close contact with the lower surface 14a. The channel sealing film 16 is desirably formed of a material, including an adhesive compound, that has a low self-fluorescent property. In this respect, a transparent film made of a resin such as a cycloolefin polymer, polyester, polypropylene, polyethylene or acrylic is suitable but is not limited thereto. Further, the channel sealing film 16 may be formed of a plate-like glass or resin. Since rigidity can be expected in this case, the channel sealing film 16 is useful for preventing warpage and deformation of the reaction processing vessel 10.

A first air communication port 24 communicating with one end 12a of the channel 12 is formed in the substrate 14. In the same way, a second air communication port 26 communicating with the other end 12b of the channel 12 is formed. The pair, the first air communication port 24 and the second air communication port 26, is formed so as to be exposed on the lower surface 14a of the substrate 14. That is, a surface on which the pair, the first air communication port 24 and the second air communication port 26, are exposed is the same as a surface on which the channel 12 is formed.

A first filter 28 is provided between the first air communication port 24 and one end 12a of the channel 12 in the substrate 14. A second filter 30 is provided between the second air communication port 26 and the other end 12b of the channel 12 in the substrate 14. The pair, the first filter 28 and the second filter 30, provided at respective ends of the channel 12, has good low impurity characteristics and also allows only air to pass therethrough so as to prevent contamination so that the amplification of target DNA and the detection of the amplification are not interrupted by PCR or so that the quality of the target DNA does not deteriorate. As a filter material, for example, a material obtained by subjecting polyethylene to a water repellent treatment can be used. Alternatively, a known material can be selected as long as the material has the above function. Regarding the dimensions of the first filter 28 and the second filter 30, the first filter 28 and the second filter 30 are formed so as to fit without any gap in a filter installation space formed in the substrate 14 and may have, for example, a diameter of 4 mm and a thickness of 2 mm. Further, the channel 12 has two systems immediately before the second filter. There are cases where a part of an evaporated sample turns into droplets and adheres to the inside of the channel, and droplets that have the adhered may prevent the liquid delivery of a sample particularly near the second filter 30, which is expected to be maintained at a relatively high temperature. Thus, the two systems are present in order to compensate for this.

The channel 12 is provided with a reaction region where the control of temperatures of a plurality of levels is possible by a reaction processor described later between the pair, the first air communication port 24 and the second air communication port 26. A thermal cycle can be applied to a sample by moving the sample such that the sample continuously reciprocates in the reaction region where the temperatures of a plurality of levels are maintained.

When the reaction processing vessel 10 is mounted on a reaction processor described later, the reaction region of the channel 12 includes a reaction region (hereinafter referred to as "high temperature region 36") maintained at a relatively high temperature (about 95° C.) and a reaction region (hereinafter referred to as "medium temperature region 38")

maintained at a temperature (about 62° C.) lower than that of the high temperature region 36. The high temperature region 36 is located on the right side of the figure page in the channel 12, and one end thereof communicates with the second air communication port 26 via the second filter 30 and a connection channel 261 between the second air communication port 26 and the second filter 30 while the other end communicates with the medium temperature region 38 via a connection channel 40. The medium temperature region 38 is located in the center of the figure page in the channel 12, and one end thereof communicates with the high temperature region 36 via the connection channel 40 while the other end communicates with a low temperature region 34 described later via a connection region 41.

The high temperature region 36 and the medium temperature region 38 each include a serpiginous shape channel where a turn is continuously made by combining curved portions and straight portions. In a case where a serpiginous shape channel is used as described above, an effective area that is limited such as that of a heater or the like constituting a temperature control means described later can be effectively used, and there are advantages that temperature variance in the reaction region is easily reduced and that the substantial size of the reaction processing vessel can be reduced, contributing to the downsizing of the reaction processor. Meanwhile, the connection channel 40 may be a linear channel.

The channel 12 further includes a region (hereinafter referred to as "low temperature region 34") maintained at a temperature that is lower than that of the medium temperature region 38. In the low temperature region, the temperature may be controlled to be maintained at a temperature lower than that in the medium temperature region. However, the temperature does not need to be particularly controlled. The low temperature region 34 is located on the left side of the figure page in the channel 12, and one end thereof communicates with the first air communication port 24 via the first filter 28 and a connection channel 241 between the first air communication port 24 and the first filter 28 while the other end communicates with the medium temperature region 38 via a connection region 41.

The low temperature region 34 is used for so-called dispensing, which is the extraction of a predetermined amount of sample. The low temperature region 34 includes a dispensing channel 42 for defining a predetermined amount of the sample, two branch channels (a first branch channel 43 and a second branch channel 44) branching from the dispensing channel 42, a first sample introduction port 45 arranged at an end of the first branch channel 43, and a second sample introduction port 46 arranged at an end of the second branch channel 44. The first sample introduction port 45 communicates with the dispensing channel 42 via the first branch channel 43. The second sample introduction port 46 communicates with the dispensing channel 42 via the second branch channel 44. The dispensing channel 42 is a serpiginous shape channel in order to dispense a predetermined amount of the sample using a minimum area. The first sample introduction port 45 and the second sample introduction port 46 are formed so as to be exposed on the upper surface 14b of the substrate 14. That is, a surface on which the first sample introduction port 45 and the second sample introduction port 46 are exposed is a surface opposite to the surface on which the channel 12 is formed. When a branch point at which the first branch channel 43 branches from the dispensing channel 42 is defined as a first branch point 431 and a branch point at which the second branch channel 44 branches from the dispensing channel 42 is defined as a second branch point 441, the volume of the sample to be subjected to PCR is almost determined by the volume inside the dispensing channel 42 between the first branch point 431 and the second branch point 441.

As described above, the first filter 28 and the second filter 30 are exposed on the lower surface 14a of the substrate 14. Since the channel 12 is formed on the lower surface 14a of the substrate 14, the channel sealing film 16 for sealing the channel 12 may have an outer shape that seals the first filter 28 and the second filter 30 at the same time as shown in FIG. 1C. The corners thereof may have a round shape so that the corners are hard to be peeled off. In this embodiment, a polypropylene film 9795 manufactured by 3M Co., Ltd., was used as the channel sealing film 16. Further, the first air communication port 24 and the second air communication port 26 are also exposed on the lower surface 14a of the substrate 14, and the first sealing film 18 different from the channel sealing film 16 is used in order to seal these communication ports as shown in FIG. 1C. Further, in order to seal the first sample introduction port 45, the second sample introduction port 46, and the connection channels 241 and 261, the second sealing film 20 is attached to the upper surface 14b of the substrate 14 as shown in FIG. 1A. In a state where the first sealing film 18 and the second sealing film 20 are attached in addition to the channel sealing film 16, the entire channel forms a closed space.

In the reaction processor 100 according to the present embodiment, a pressurization pump (described later) that is a liquid feeding means is connected only to the first air communication port 24, and the second air communication port 26 is open to atmospheric pressure. The connection between the pressurization pump and the first air communication port 24 and the opening of the second air communication port 26 are realized by peeling off the parts of the first sealing film 18 that correspond to these communication ports so as to expose the first air communication port 24 and the second air communication port 26. The first sealing film 18 may be formed with a non-adhesive tab 181 that is easy to hold with fingers at the time of peeling off so that the first sealing film 18 can be easily peeled off. Alternatively, the opening of these communication ports may be realized by piercing the corresponding parts of the first air communication port 24 and the second air communication port 26 of the first sealing film 18 with a needle or the like. In this case, the first sealing film 18 is preferably a film made of a material that is easily perforated by a needle and/or have a thickness that is easily perforated by a needle. Conversely, the second air communication port 26 may be connected to a pressurization pump, and the first air communication port 24 may be open to atmospheric pressure.

Introduction of a sample into the reaction processing vessel 10 through the first sample introduction port 45 and the second sample introduction port 46 is performed by once peeling the parts of the second sealing film 20 that correspond to the first sample introduction port 45 and the second sample introduction port 46 from the substrate 14 within a range where the connection channels 241 and 261 are not exposed, and, after the introduction of a predetermined amount of sample, the second sealing film 20 is put back being attached to the upper surface 14b of the substrate 14 again. Therefore, as the second sealing film 20, a film is desired that is sticky enough to hold up through several cycles of attaching and peeling. Alternatively, as the second sealing film 20, a new film may be attached after the introduction of a sample. In this case, the importance of the property related to repetitive attaching and peeling can be lessened.

In the same way as in the channel sealing film 16, the first sealing film 18 and the second sealing film 20 may have an adhesive layer or a functional layer exhibiting stickiness or adhesiveness by pressing that is formed on one of the principal surfaces thereof. In this respect, a transparent film made of a resin such as a cycloolefin polymer, polyester, polypropylene, polyethylene or acrylic is suitable but is not limited thereto. As described above, the property such as stickiness or the like desirably do not degrade to such an extent that the use is affected even after attaching and peeling of multiple times. However, in a case where a new film is attached after the peeling and the introduction of a sample or the like, the importance of this property related to the attaching and peeling can be lessened. In the present embodiment, a polypropylene film 9793 manufactured by 3M Co., Ltd., or the like was used as the first sealing film 18 and the second sealing film 20.

An explanation will be given next regarding a method of using the reaction processing vessel 10 formed as described above. First, a sample to be amplified through a thermal cycle is prepared. The sample includes, for example, those obtained by adding a fluorescent probe, a thermostable enzyme and four types of deoxyribonucleoside triphosphates (dATP, dCTP, dGTP, dTTP) as PCR reagents to a mixture containing one or more types of DNA. Further, a primer that specifically reacts to DNA subjected to reaction treatment is mixed. Commercially available real-time PCR reagent kits and the like can be also used.

Then, only the parts of the second sealing film 20 that correspond to the first sample introduction port 45 and the second sample introduction port 46 are peeled from the substrate 14 within a range where the connection channels 241 and 261 are not exposed so as to expose and open the first sample introduction port 45 and the second sample introduction port 46. The second sealing film 20 may be formed with a non-adhesive tab 201 that is easy to hold with fingers at the time of peeling off so that the second sealing film 20 can be easily peeled off. The operator holds the tab 201 and peels off the second sealing film 20 up to, for example, a dotted line (A) shown in FIG. 1A.

Figure 4:
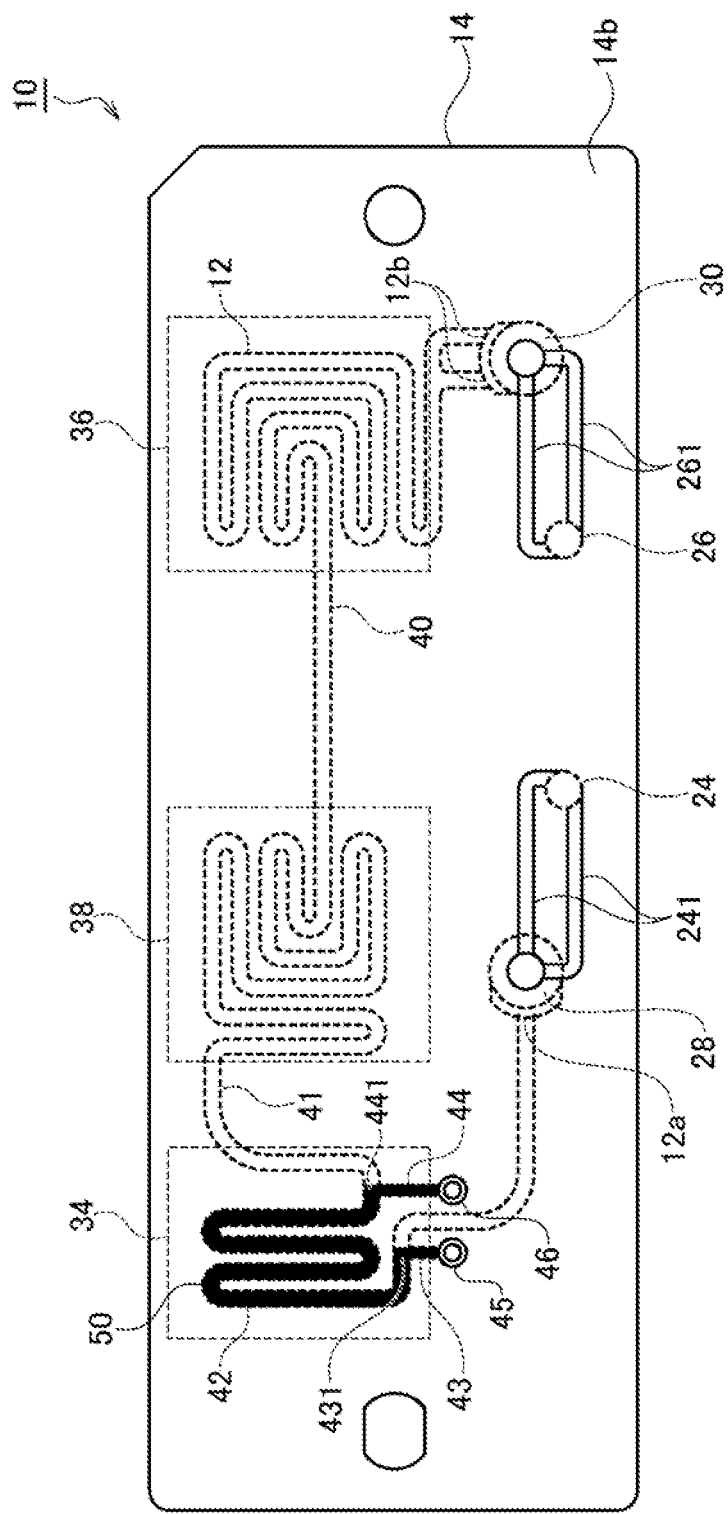
FIG. 4 is a diagram schematically showing a state where a sample is introduced into the reaction processing vessel.

The sample is then introduced to a sample introduction port by a pipetter, a dropper, a syringe, or the like. FIG. 4 schematically shows a state where a sample 50 is introduced into the reaction processing vessel 10. In FIG. 4, the description of a film and the like is omitted in order to explain the relationship between the sample 50 that has been introduced and the reaction processing vessel 10. The sample 50 is introduced into the dispensing channel 42 through either one of the first sample introduction port 45 and the sample introduction port 46. The method for the introduction is not limited to this. Alternatively, for example, an appropriate amount of the sample 50 may be directly introduced using a pipette or a dropper. The excess portion of the sample introduced through either one of the sample introduction ports that exceeds the volume of the branch channel becomes accumulated at the other one of the sample introduction ports. Therefore, in order to utilize the sample introduction port part as a kind of reservoir, the sample introduction port part may be made to have a certain space. As will be described later, the sample 50 loaded into the dispensing channel 42 between the first branch point 431 and the second branch point 441 undergoes PCR by effect of controlled pressure through the first air communication port 24. In this manner, the low temperature region 34 of the reaction processing vessel 10 performs a dispensing function of extracting a predetermined amount of sample.

Next, the second sealing film 20 is attached to the substrate 14 again such that the first sample introduction port 45 and the second sample introduction port 46 are sealed. Since the tab 201 becomes unnecessary after the sealing, the tab 201 may be cut off in advance. Instead of the second sealing film 20 that has been peeled off, a new second sealing film 20 may be attached. This completes the introduction of the sample 50 into the reaction processing vessel 10.

The above-mentioned dispensing function in the reaction processing vessel is not to prevent introduction of the sample while precisely dispensing the sample with a pipetter. In this case, since dispensing is performed in advance, the tip of the sample introduced from one of the sample introduction ports does not have to reach the branch point on the other sample introduction port side.

Figure 5:
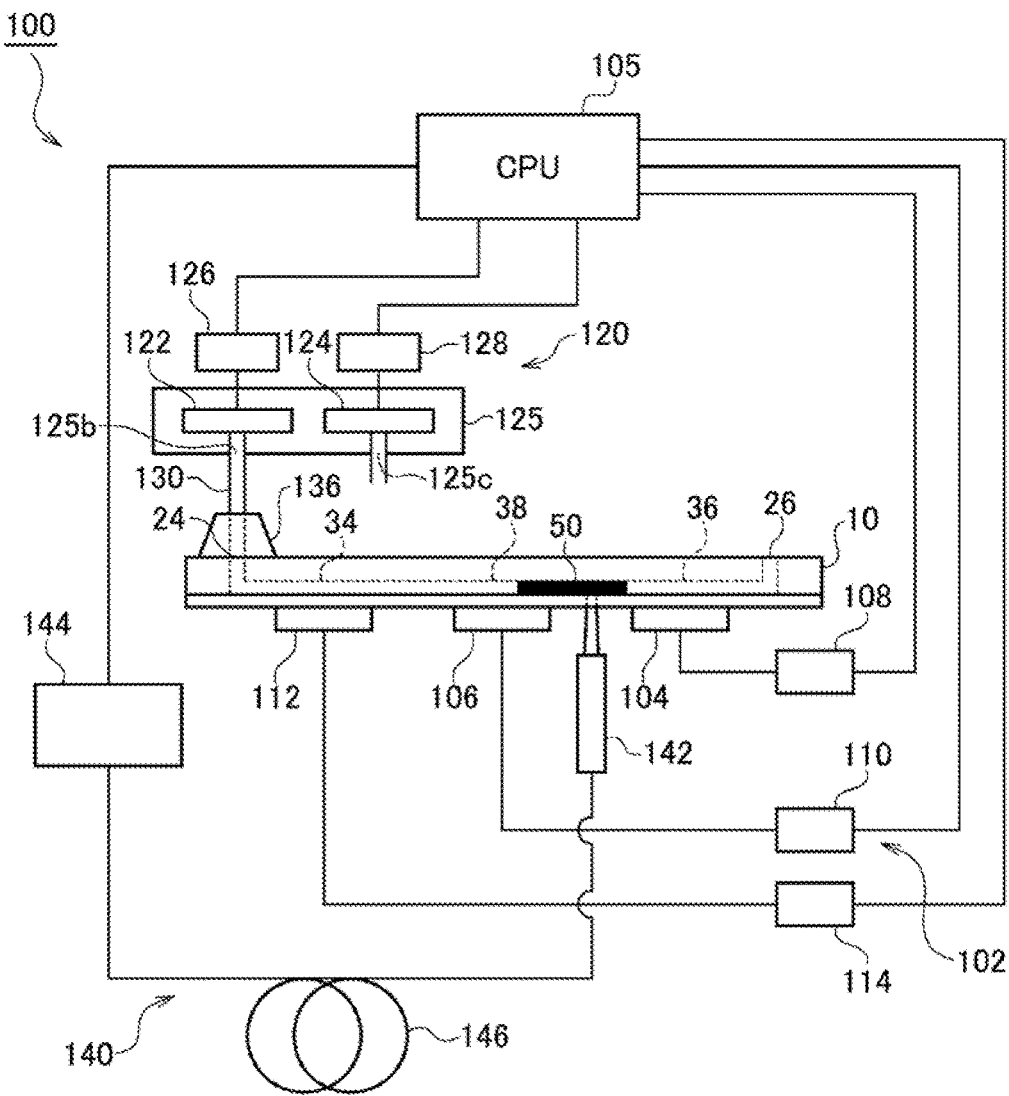
FIG. 5 is a schematic diagram for explaining a reaction processor according to an embodiment of the present invention.

FIG. 5 is a schematic diagram for explaining a reaction processor 100 according to the embodiment of the present invention. In the form of the reaction processing vessel 10 described above, the channel 12, the first air communication port 24, and the second air communication port 26 exist on the surface 14a of the reaction processing vessel 10. Thus, the channel 12 and a connection part from a liquid feeding system. 120 are actually arranged on the same side of the substrate 14. However, it should be noted, in order to facilitate the understanding of the drawings for the sake of explanation, that the channel 12 and the connection part from the liquid feeding system 120 are intentionally described being arranged on different sides of the substrate 14 and that the existence of each temperature region between a pair of air communication ports is expressed in a conceptually easy-to-understand manner.

The reaction processor 100 according to the present embodiment includes reaction processing vessel installation unit (not shown) in which the reaction processing vessel 10 is installed, a temperature control system 102, and a CPU 105. As shown in FIG. 5, relative to the reaction processing vessel 10 installed in the reaction processing vessel installation unit, the temperature control system 102 is formed so as to be able to accurately maintain and control the temperature of the high temperature region 36 in the channel 12 of the reaction processing vessel 10 to be about 95° C., the temperature of the medium temperature region 38 to be about 62° C., and the temperature of the low temperature region 34 to be about 30° C. to 40° C.

The temperature control system 102 is for adjusting the temperature of each temperature region of the thermal cycle region and is specifically provided with a high temperature heater 104 for heating the high temperature region 36 of the channel 12, a medium temperature heater 106 for heating the medium temperature region 38 of the channel 12, a low temperature heater 112 for heating the low temperature region 34 of the channel 12, a temperature sensor (not shown) such as, for example, a thermocouple or the like for measuring the actual temperature of each temperature region, a high temperature heater driver 108 for controlling the temperature of the high temperature heater 104, a medium temperature heater driver 110 for controlling the temperature of the medium temperature heater 106, and a low temperature heater driver 114 for controlling the temperature of the low temperature heater 112. Information on the actual temperature measured by the temperature sensor is sent to the CPU 105. Based on the information on the actual temperature of each temperature region, the CPU 105 controls each heater driver such that the temperature of each temperature region heated by each heater becomes a predetermined temperature. Each heater may be, for example, a resistance heating element, a Peltier element, or the like. The temperature control system 102 may be further provided with other components for improving the temperature controllability of each temperature region.

The reaction processor 100 according to the present embodiment is further provided with a liquid feeding system 120 for discharging and sucking air in order to move and stop the sample 50 inside the channel 12 of the reaction processing vessel 10.

Figure 6:
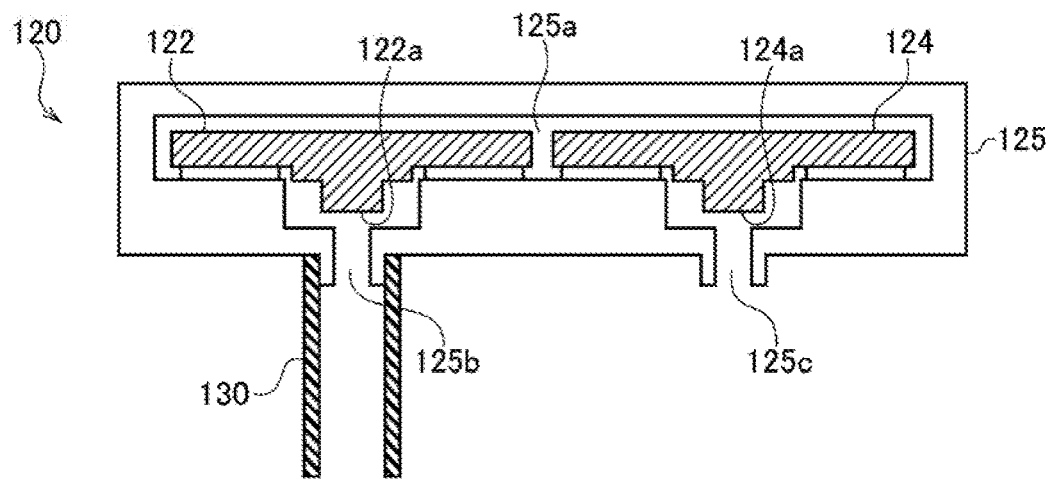
FIG. 6 is a schematic view for explaining the configuration of a liquid feeding system.

FIG. 6 is a schematic view for explaining the configuration of the liquid feeding system 120. The liquid feeding system 120 is provided with a chamber 125, a first pump 122, a second pump 124, a first pump driver 126 for driving the first pump 122, a second pump driver 128 for driving the second pump 124, and a tube 130. The first pump driver 126 and the second pump driver 128 are controlled by the CPU 105.

The chamber 125 has an internal space 125a having a constant volume and a first air vent 125b and a second air vent 125c that allow the internal space 125a to communicate with the outside. A first pump 122 and a second pump 124 are arranged in the internal space 125a of the chamber 125. The first pump 122 and the second pump 124 may be, for example, micro blower pumps each comprising a diaphragm pump. As the first pump 122 and the second pump 124, for example, micro blower pumps (MZB1001 T02 model) manufactured by Murata Manufacturing Co., Ltd., or the like can be used. The first pump 122 is arranged such that the air discharged from the discharge port 122a is exhausted from the first air vent 125b of the chamber 125. The second pump 124 is arranged such that the air discharged from the discharge port 124a is exhausted from the second air vent 125c of the chamber 125.

The first air vent 125b of the chamber 125 communicates with one of the pair of air communication ports of the reaction processing vessel 10 that is farther away from the high temperature region 36 via the tube 130, that is, the first air communication port 24. On the other hand, the second air vent 125c of the chamber 125 is opened to atmospheric pressure. Under such a connection state, the CPU 105 controls the first pump 122 and the second pump 124 via the first pump driver 126 and the second pump driver 128 such that the first pump 122 and the second pump 124 perform the air discharging operation alternately. When the discharging operation of the first pump 122 is performed and the second pump 124 is stopped, the inside of the tube 130 has a positive pressure, and air is discharged from the tube 130 to the first air communication port 24 of the reaction processing vessel 10. On the other hand, when the first pump 122 is stopped and the discharging operation of the second pump 124 is performed, air is discharged from the second air vent 125c of the chamber 125 causing the inside of the internal space 125a of the chamber 125 to have a negative pressure. Thus, the inside of the tube 130 also has a negative pressure, and air is sucked into the tube 130 from the first air communication port 24 of the reaction processing vessel 10. By the discharging or suction of air by the tube 130, the sample 50 can be moved in a reciprocating manner in the channel so as to be repeatedly exposed to each temperature region of the channel 12 of the reaction processing vessel 10. As a result, a thermal cycle can be applied to the sample 50. More specifically, target DNA in the sample 50 is selectively amplified by repeatedly applying a step of denaturation in the high temperature region 36 and a step of annealing and elongation in the medium temperature region 38. In other words, the high temperature region 36 can be considered to be a denaturation temperature region, and the medium temperature region 38 can be considered to be an annealing and elongation temperature region. The time for staying in each temperature region can be appropriately set by changing the time during which the sample 50 stops at a predetermined position in each temperature region.

The reaction processor 100 according to the present embodiment is further provided with a fluorescence detector 140. As described above, a predetermined fluorescent probe is added to the sample 50. Since the intensity of a fluorescence signal emitted from the sample 50 increases as the amplification of the DNA proceeds, the intensity value of the fluorescence signal can be used as an index serving as a decision-making factor for the progress of the PCR or the termination of the reaction.

As the fluorescence detector 140, an optical fiber-type fluorescence detector FLE-510 manufactured by Nippon Sheet Glass Co., Ltd., can be used, which is a very compact optical system that allows for rapid measurement and the detection of fluorescence regardless of whether the place is a lighted place or a dark place. This optical fiber-type fluorescence detector allows the wavelength characteristic of the excitation light/fluorescence to be tuned such that the wavelength characteristic is suitable for the characteristic of fluorescence emitted from the sample 50 and thus allows an optimum optical and detection system for a sample having various characteristics to be provided. Further, the optical fiber-type fluorescence detector is suitable for detecting fluorescence from a sample existing in a small or narrow region such as a channel because of the small diameter of a ray of light brought by the optical fiber-type fluorescence detector and is also excellent in response speed.

The optical fiber-type fluorescence detector 140 is provided with an optical head 142, a fluorescence detector driver 144, and an optical fiber 146 connecting the optical head 142 and the fluorescence detector driver 144. The fluorescence detector driver 144 includes a light source for excitation light (LED, a laser, or a light source adjusted to emit other specific wavelengths), an optical fiber-type multiplexer/demultiplexer and a photoelectric conversion device (PD, APD, or a light detector such as a photomultiplier) (neither of which is shown), and the like and formed of a driver or the like for controlling these. The optical head 142 is formed of an optical system such as a lens and has a function of directionally irradiating the sample with excitation light and collecting fluorescence emitted from the sample. The collected fluorescence is separated from the excitation light by the optical fiber-type multiplexer/demultiplexer inside the fluorescence detector driver 144 through the optical fiber 146 and converted into an electric signal by the photoelectric conversion element.

In the reaction processor 100 according to the present embodiment, the optical head 142 is arranged such that fluorescence from the sample 50 in the channel connecting the high temperature region 36 and the medium temperature region 38 can be detected. Since the reaction progresses while the sample 50 is repeatedly moved in a reciprocating manner in the channel such that predetermined DNA contained in the sample 50 is amplified, by monitoring a change in the amount of detected fluorescence, the progress of the DNA amplification can be learned in real time. Further, in the reaction processor 100 according to the present embodiment, an output value from the fluorescence detector 140 is utilized for controlling the movement of the sample 50, as described later. The fluorescence detector is not limited to an optical fiber-type fluorescence detector as long as the fluorescence detector exhibits the function of detecting fluorescence from a sample.

Referring to FIG. 5, the motion of applying a thermal cycle to the sample 50 by the reaction processor 100 will be described. The reaction processing vessel 10 into which the sample 50 is introduced is set in the reaction processor 100, the first air communication port 24 of the reaction processing vessel 10 is connected to the first air vent 125b of the chamber 125 via the tube 130, and the second air communication port 26 of the reaction processing vessel 10 is opened to atmospheric pressure. Thereafter, by operating only the first pump 122, the inside of the tube 130 has a positive pressure, and the sample 50 in the low temperature region 34 is moved to the medium temperature region 38 or the high temperature region 36. When the sample 50 is moved from the high temperature region 36 toward the medium temperature region 38, only the second pump 124 is operated. Thereby, the inside of the tube 130 results in having a negative pressure, and the sample 50 thus moves from the high temperature region 36 toward the medium temperature region 38. On the other hand, when the sample 50 is moved from the medium temperature region 38 toward the high temperature region 36, only the first pump 122 is operated. Thereby, the inside of the tube 130 results in having a positive pressure, and the sample 50 thus moves from the medium temperature region 38 toward the high temperature region 36. Thereafter, by alternately operating the first pump 122 and the second pump 124, the sample 50 is continuously moved reciprocally between the high temperature region 36 and the medium temperature region 38, and a thermal cycle can thus be applied to the sample 50.

Figure 7:
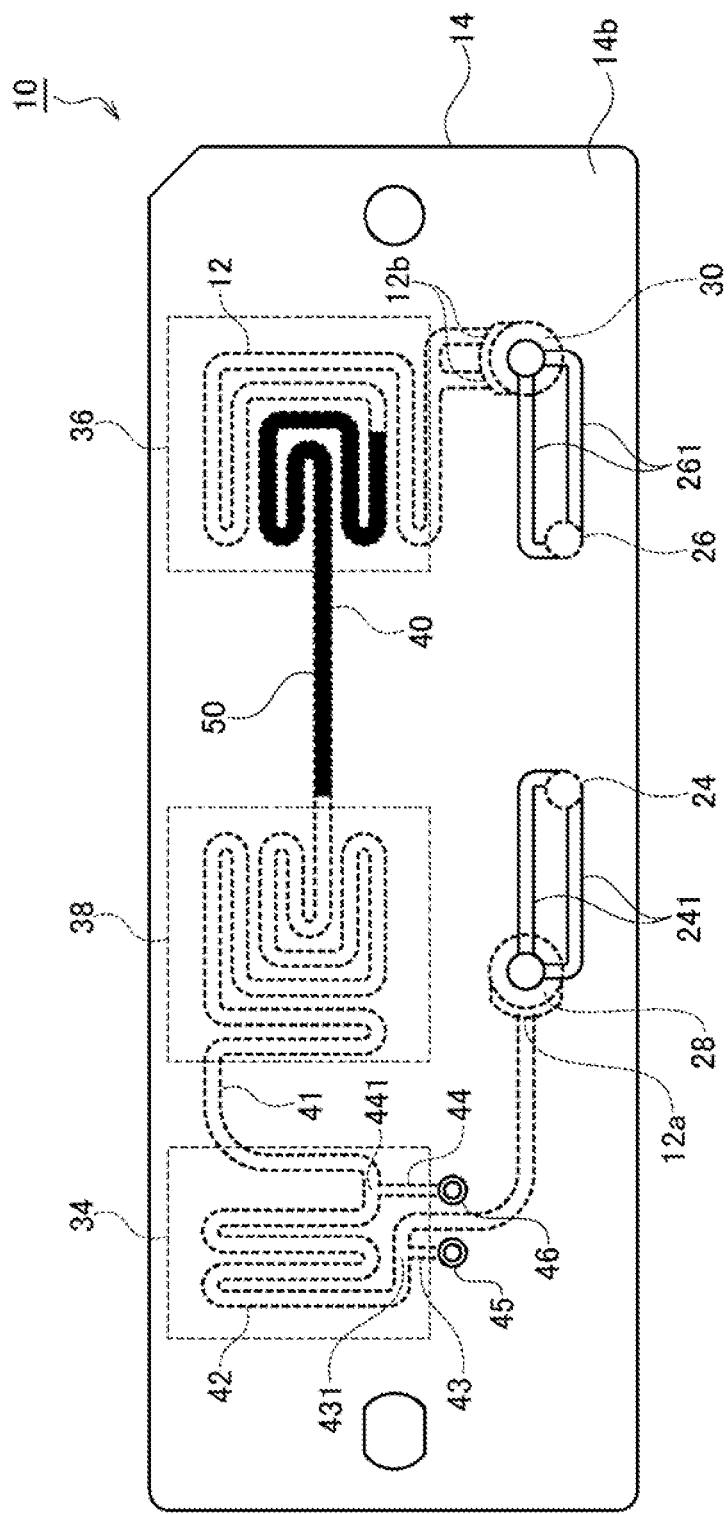
FIG. 7 is a diagram showing a state where a thermal cycle is applied to a sample inside a channel of the reaction processing vessel.

FIG. 7 is a diagram showing a state where a thermal cycle is applied to a sample inside a channel of the reaction processing vessel 10. In the reaction processing vessel 10 shown in FIG. 7, the sample 50 loaded into the dispensing channel 42 between the first branch point 431 and the second branch point 441 in the low temperature region 34 is moved between the high temperature region 36 and the medium temperature region 38.

As explained above, in the reaction processor 100 according to the present embodiment, the liquid feeding system 120 is connected only to the first air communication port 24 located far from the high temperature region 36 via the tube 130, and the second air communication port 26 located close to the high temperature region 36 is opened to atmospheric pressure. Carryover in PCR is considered to be caused by a part of amplified DNA fragments floating or adhering in the form of aerosol or the like in the air in the tube 130 and being mixed into the sample inside the reaction processing vessel 10. It is considered that the aerosols of DNA fragments are often generated when a liquid mixed with the DNA fragments is vaporized. Naturally, the vaporization phenomenon is more likely to occur as the vapor pressure of the sample (solution) is higher. Thus, by opening the air communication port on the high temperature region 36 side (that is, the second air communication port 26 close to the high temperature region 36) where the vaporization phenomenon is likely to occur relatively and allowing the liquid feeding system 120 to communicate only with the air communication port on the medium temperature region 38 side (that is, the first air communication port 24 far from the high temperature region 36) where the vaporization phenomenon is unlikely to occur relatively, the DNA fragments are unlikely to be brought inside the tube 130 as aerosol, and carryover can thus be prevented or at least suppressed.

In order to confirm the effect of the reaction processor 100 formed as described above, an experiment was performed where a specific bacterial strain was amplified by PCR using the reaction processor 100 according to the present embodiment. The preparation of a sample to be subjected to PCR was performed as follows. Entries in a document "*Escherichia coli* rapid measuring method using genetic examination method" (http://www.city.osaka.lg.jp/suido/cmsfiles/contents/0000245/245422/6_250227.pdf) published on the website of the Osaka City Waterworks Bureau were used as reference.

(i) 5'-GTG TGA TAT CTA CCC GCT TCG C-3' (SEQ ID NO: 1) was used as a forward primer, 5'-AGA ACG GTT TGT GGT TAA TCA GGA-3' (SEQ ID NO: 2) was used as a reverse primer, and 5'-FAM-TCG GCA TCC GGT CAG TGG CAG T-MGB-3' (SEQ ID NO: 3) was selected as a TaqMan (registered trademark) probe. The respective concentrations (final concentration) of the primers and the probe were 900 nM (nM: nanomolar: nanomole/liter), 900 nM and 250 nM, respectively. (ii) A template DNA in a region amplified in (i) above was prepared at a concentration of $1\times10^6$ Copies/µL upon making a request to a synthetic DNA manufacturer. A standard specimen ($1\times10^1$ to $1\times10^6$ Copies/µL) consisting of a 10-fold dilution series was prepared from this. (iii) Further, as a DNA polymerase, 0.1 U/µL of SpeedSTAR (registered trademark) HS DNA Polymerase manufactured by Takara Bio Inc., and ×10 Fast buffer I and dNTP Mix that accompanied the DNA Polymerase were mixed as described in the manual and added to the reagent. "U" representing unit in [U/µL] represents a unit of an enzymatic activity amount, and the amount of an enzyme that can convert 1 µmol ($1\times10^{-6}$ mol) of substrate per minute under optimum conditions is defined as 1 U and roughly represents the amount of enzyme. (iv) To 24 µL of this reagent, 1 µL of the standard specimen having a different concentration prepared in (ii) was added to prepare a sample. Further, a reagent to which the standard specimen was not added was prepared as a negative control sample. A negative control is a control (sample) that should result in being negative in an effect control experiment. In this case, the negative control results in the inclusion of no bacteria (negative) even when PCR is performed. The opposite of this is a positive control, which corresponds to the above-mentioned standard specimen and results in the inclusion of bacteria (positive) through PCR.

Out of samples prepared as described above, a sample containing a specimen with a concentration of $1\times10^6$ Copies/µL was used as a positive control sample, and amplification through PCR was performed alternately with a negative control sample. 15 µL of the sample was introduced into the reaction processing vessel 10 described above using a pipetter. Further, since the reaction processing vessel 10 is provided with a dispensing channel 42 that allows for dispensing, even if the reaction processing vessel 10 is changed, erroneous judgment of the result caused due to the difference in the volume of the sample in each occasion can be reduced.

The sample subjected to a thermal cycle repeats reciprocation between the high temperature region 36 and the medium temperature region 38 in the reaction processing vessel 10 described above. It was assumed that the thermal cycle condition was to hold the sample for 10 seconds in the medium temperature region 38 (annealing and elongation region) maintained at 62° C. and hold the sample for 3 seconds in the high temperature region 36 (thermal denaturation region) maintained at 95° C. This was defined as one cycle and was repeated. The temperature of the low temperature region 34 was maintained at about 30 to 40° C.

Figure 8:
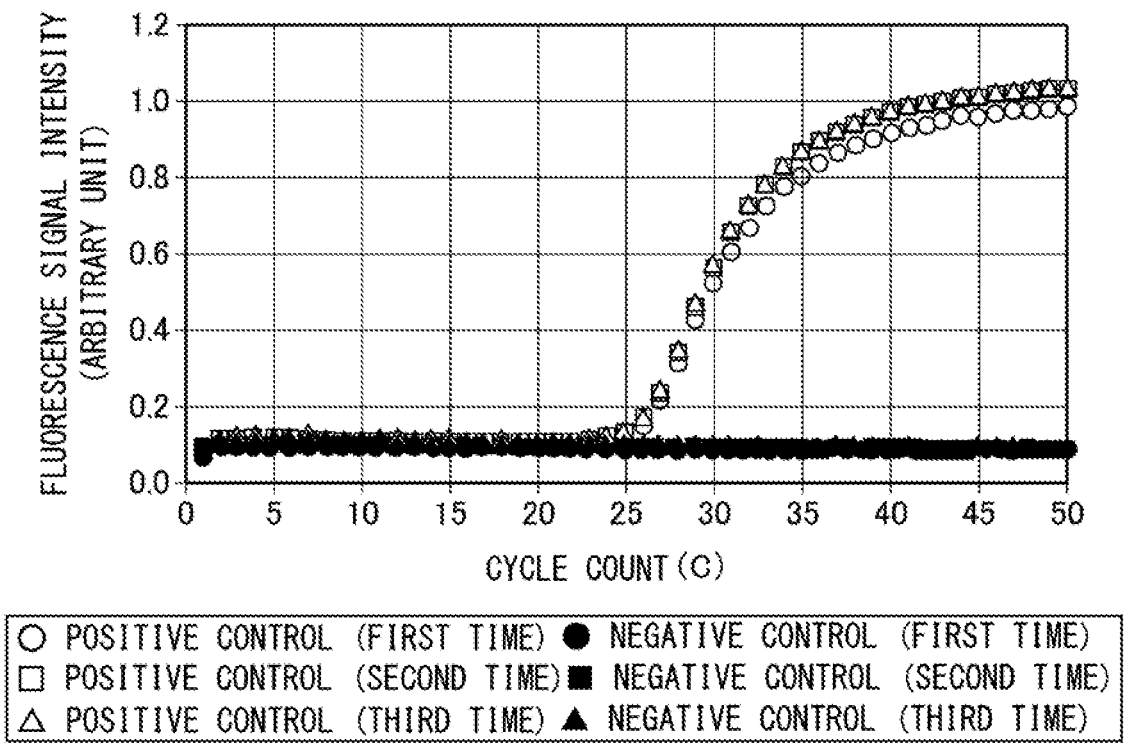
FIG. 8 is a diagram showing a PCR amplification result by the reaction processor according to the present embodiment.

FIG. 8 shows a PCR amplification result by the reaction processor 100 according to the present embodiment. In FIG. 8, the horizontal axis represents the cycle count (C), and the vertical axis represents the fluorescence signal intensity (arbitrary unit). Using the reaction processor 100 described above, the intensity of a fluorescence signal detected by the fluorescence detector 140 with respect to a cycle count was measured. As a specimen in the sample was amplified, the intensity of the fluorescence signal increased. FIG. 8 shows the results of alternately performing PCR for the positive control sample and PCR for the negative control sample three times each. As shown in FIG. 8, the fluorescence signal intensity in the case of the positive control sample rises sharply from around 26 cycles, and it can be seen that the specimen in the positive control sample was amplified. On the other hand, the fluorescence signal intensity in the case of the negative control sample was almost constant (background level) after 50 cycles, and it can be seen that carryover did not occur or was negligibly small.

Figure 9:
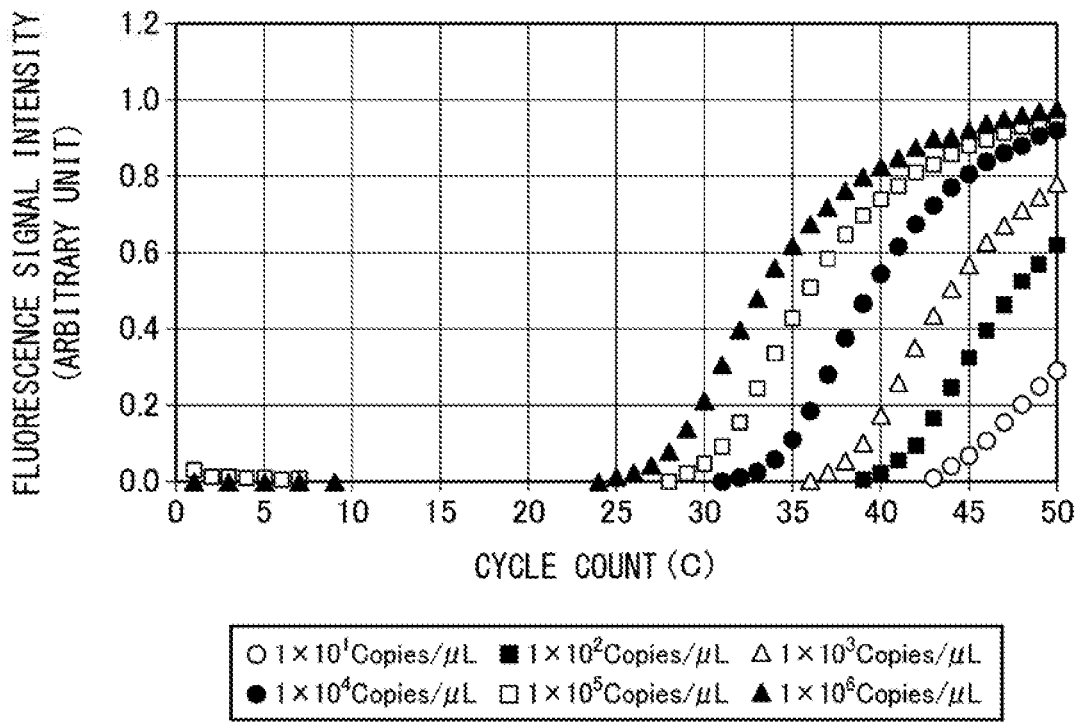
FIG. 9 is a diagram showing a PCR amplification result by the reaction processor according to the present embodiment.

FIG. 9 also shows a PCR amplification result by the reaction processor 100 according to the present embodiment. PCR was performed on a sample containing six specimens having initial concentrations of $1 \times 10^1$ to $1 \times 10^6$ Copies/µL (respectively in 10-fold increments). From FIG. 9, it can be seen that as the initial specimen concentration increases, the cycle count at which the fluorescence signal intensity rises, that is, the cycle count at which the amplification of a specimen was started decreases.

Figures 10, 11:
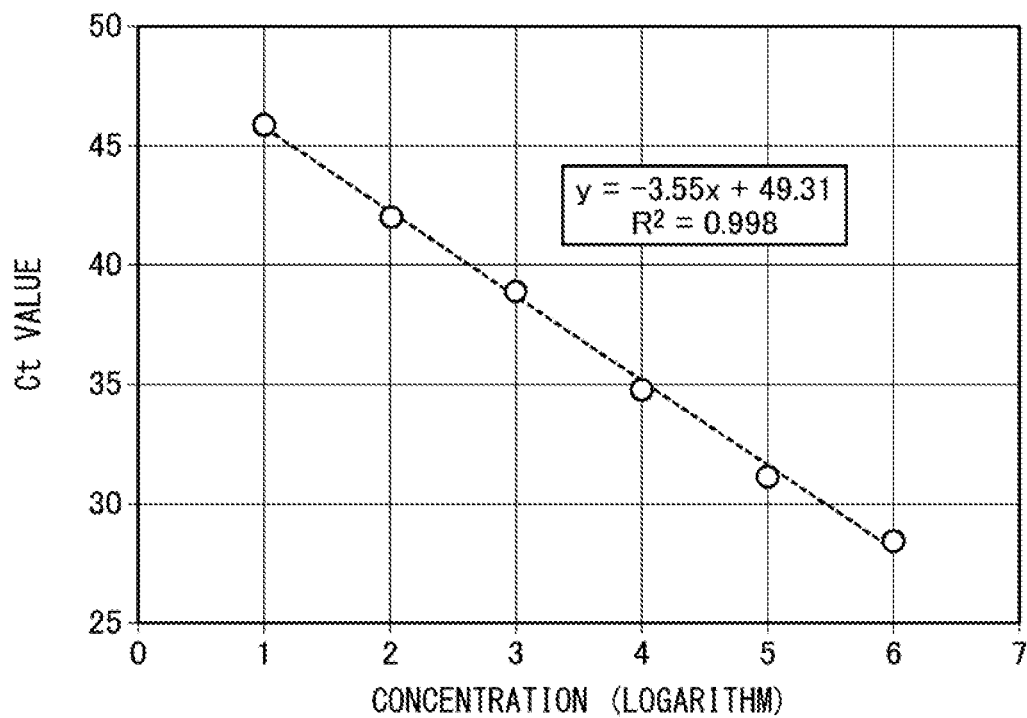
FIG. 10 is a table showing Ct values for six specimens having different initial specimen concentrations.
FIG. 11 is a diagram showing a calibration curve in which the relationship between the initial concentrations and the Ct values shown in FIG. 10 is plotted.

FIG. 10 is a table showing Ct values (threshold cycle count) for the six specimens having initial specimen concentrations of $1 \times 10^1$ to $1 \times 10^6$ Copies/µL. The Ct values were set to 10% of the plateaus of the respective amplification curves.

FIG. 11 shows a calibration curve in which the relationship between the initial concentrations and the Ct values shown in FIG. 10 is plotted. The slope (S) of the calibration curve obtained from FIG. 11 is −3.55. Further, the PCR efficiency ($10^{(-1/S)}-1$) is calculated to be 91.2%, indicating that a good PCR is being performed.

Figure 12:
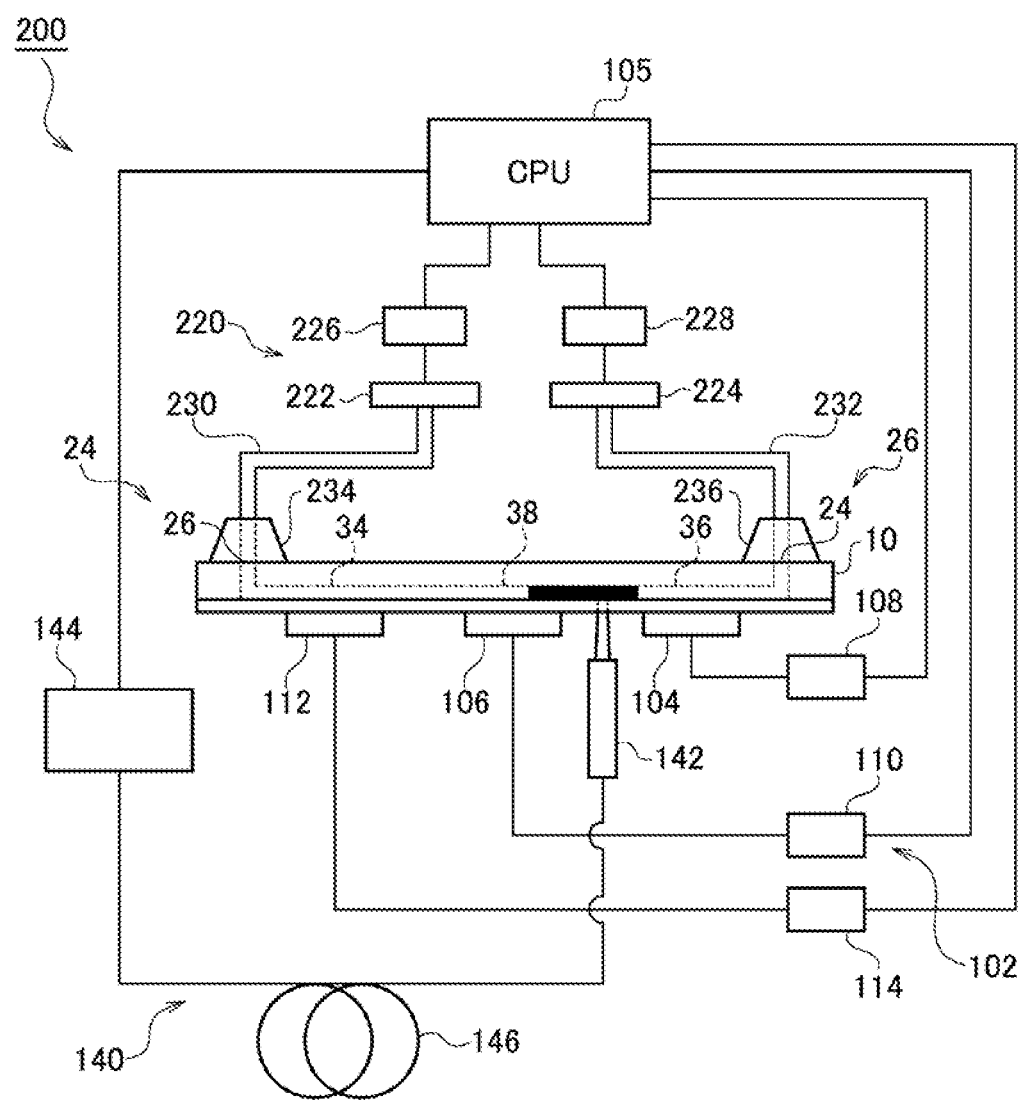
FIG. 12 is a diagram for explaining a reaction processor according to a comparative example.

A detailed description is now given of a comparative example. FIG. 12 is a diagram for explaining a reaction processor 200 according to a comparative example. In the reaction processor 200 according to this comparative example, the configuration of a liquid feeding system 220 is different from that of the liquid feeding system 120 of the reaction processor 100 shown in FIG. 5. The liquid feeding system 220 is provided with a first pump 222, a second pump 224, a first pump driver 226 for driving the first pump 222, a second pump driver 228 for driving the second pump 224, a first tube 230, and a second tube 232.

In the liquid feeding system 220, the first pump 222 and the second pump 224 are arranged not inside the chamber but in atmospheric pressure. The first air communication port 24 of the reaction processing vessel 10 communicates with a discharge port of the first pump 222 via the first tube 230, and the second air communication port 26 of the reaction processing vessel 10 communicates with a discharge port of the second pump 224 via the second tube 232. Packing materials 234 and 236 or seals for securing airtightness may be arranged at the junction of the first air communication port 24 and the first tube 230 and the junction of the second air communication port 26 and the second tube 232.

In the liquid feeding system 220 formed and arranged in this manner, a sample 50 can be reciprocated inside the channel 12 of the reaction processing vessel 10 by alternately operating the first pump 222 and the second pump 224 for discharging.

Figure 13:
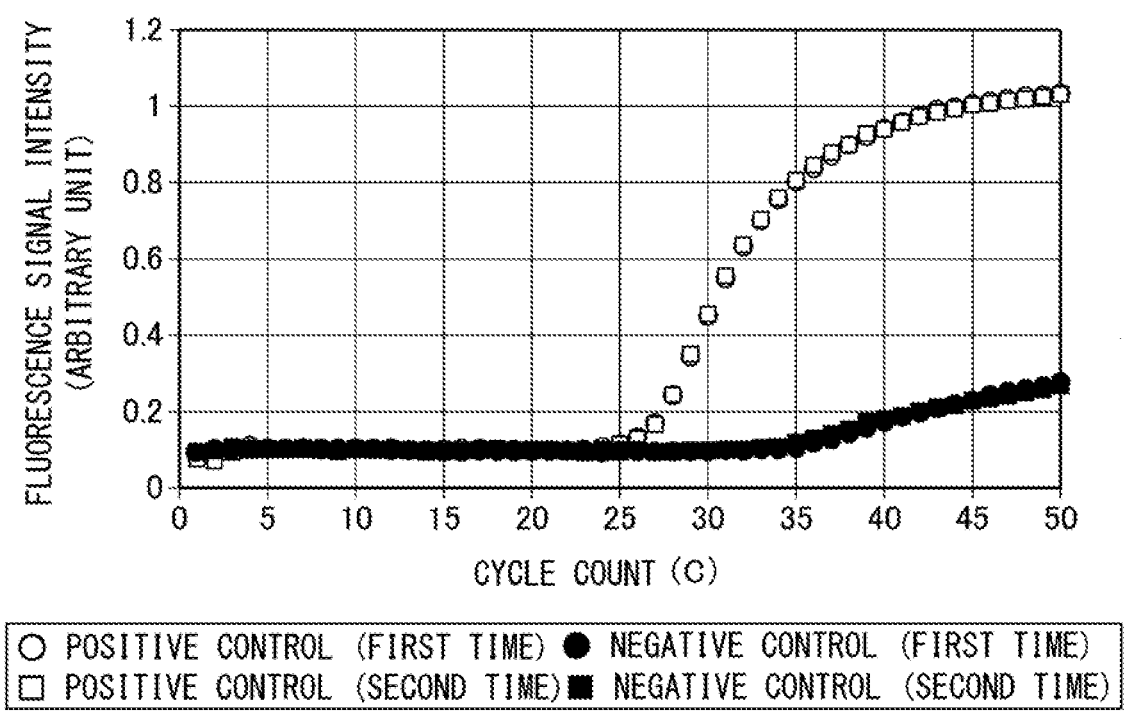
FIG. 13 is a diagram showing a PCR amplification result by the reaction processor according to the comparative example.

FIG. 13 shows a PCR amplification result by the reaction processor 200 according to the comparative example. In FIG. 13, the horizontal axis represents the cycle count (C), and the vertical axis represents the fluorescence signal intensity (arbitrary unit). Regarding the sample, a positive control and a negative control obtained through preparation performed in the same manner as in the experiment described in FIG. 8 were prepared, and then PCR was performed twice alternately. From amplification curves shown in FIG. 13, it can be seen that the same results as the amplification results shown in FIG. 8 are obtained for the positive control while the fluorescence signal intensity starts to rise at 30 cycles or more for the negative control. The respective Ct values of the first negative control and the second negative control were 41.89 and 41.41, respectively. The level of the Ct values corresponds to the initial specimen concentration of approximately $1 \times 10^2$ Copies/µL in the calibration curve shown in FIG. 11. In the reaction processor 200 according to the comparative example, when the initial specimen concentration is $1 \times 10^2$ Copies/µL or less, it may not be known whether the result is actually positive or is caused by detection due to carryover.

On the other hand, in the reaction processor 100 according to the embodiment of the present invention, such carryover can be prevented, so that quantification can be performed even at an initial concentration of, for example, $1 \times 10^1$ copies/µL level or lower.

As can be seen from the amplification result shown in FIG. 8, in the reaction processor 100 according to the present embodiment in which the liquid feeding system 120 communicates only with the first air communication port 24 of the reaction processing vessel 10, no carryover occurred in the negative control. On the other hand, as can be seen from the amplification result shown in FIG. 13, in the reaction processor 200 according to the comparative example in which the liquid feeding system 220 communicates with the first air communication port 24 and the second air communication port 26 of the reaction processing vessel 10, carryover occurred in the negative control. Therefore, from these experimental results, it is considered that the carryover in PCR was caused due to DNA fragments amplified by the positive control floating as aerosol in the air inside the tube and being mixed into the sample in the reaction processing vessel 10.

In the present embodiment, filters are provided at respective ends of the channel 12 of the reaction processing vessel 10. These filters are effective in preventing or suppressing carryover. In particular, considering that DNA fragments are less likely to be brought into the tube 130 as aerosol, it is desirable that a filter (that is, the first filter 28) be provided at least at one end 12a of the channel that is farther away from the high temperature region 36.

Figure 14:
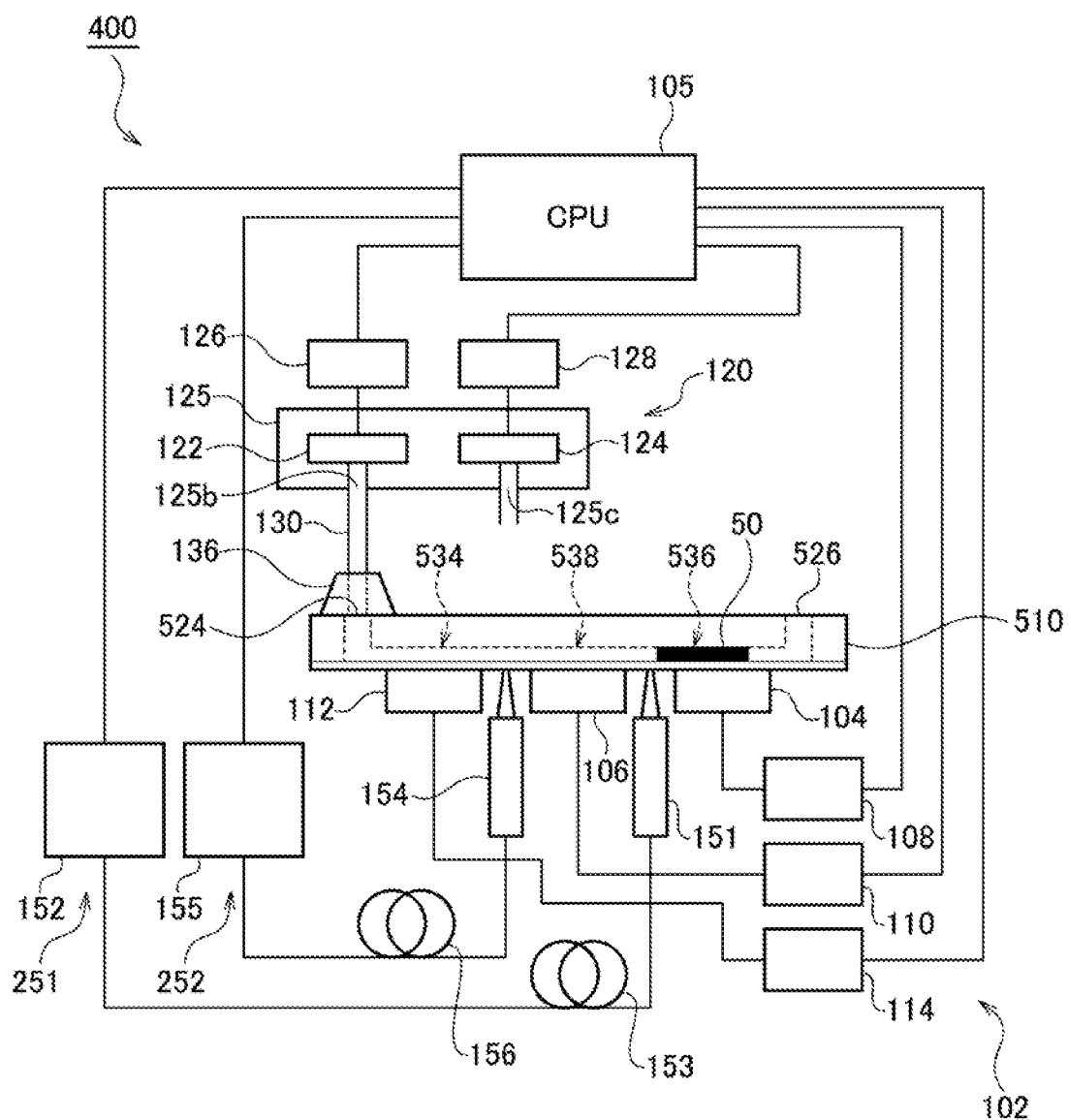
FIG. 14 is a diagram for explaining another embodiment of the reaction processor.

FIG. 14 is a diagram for explaining another embodiment of the reaction processor. A reaction processor 400 shown in FIG. 14 is a device for performing a thermal cycle on a reaction processing vessel 510 having reaction regions of three levels: a high temperature region 536; a medium temperature region 538; and a low temperature region 534. The reaction processing vessel 510 includes a first air communication port 524 and a second air communication port 526 at respective ends of a channel.

The reaction processor 400 includes two fluorescence detectors (a first fluorescence detector 251 and a second fluorescence detector 252). The first fluorescence detector 251 includes: a first optical head 151 for detecting fluorescence from a sample 50 passing through a region between the high temperature region 536 and the medium temperature region 538 of the channel of the reaction processing vessel 510; a first fluorescence detector driver 152; and a first optical fiber 153 connecting the first optical head 151 and the first fluorescence detector driver 152. The second fluorescence detector 252 includes: a second optical head 154 for detecting fluorescence from a sample 50 passing through a region between the medium temperature region 538 and the low temperature region 534 of the channel of the reaction processing vessel 510; a second fluorescence detector driver 155; and a second optical fiber 156 connecting the second optical head 154 and the second fluorescence detector driver 155.

Also for the reaction processing vessel 510 having the reaction region of three levels as shown in FIG. 14, by connecting the liquid feeding system 120 to the first air communication port 524, which is an air communication port farther away from the high temperature region 536, via the tube 130 and opening the second air communication port 526, which is the air communication port closer to the high temperature region 536, to atmospheric pressure, an effect of preventing or suppressing carryover is obtained.

In the reaction processor 400, for example, it is assumed that the thermal cycle condition is to hold the sample 50 for 3 seconds in a high temperature region 536 maintained at 95° C., hold the sample 50 for 10 seconds in the low temperature region 534 maintained at 55° C., and hold the sample 50 for 10 seconds in the medium temperature region 538 maintained at 70° C. This is defined as one cycle and repeated. When PCR is carried out in the reaction regions of three levels, it is advantageous in terms of ease of the preparation of the sample 50, the expansion of the selection range of additives, and the like. Further, for the activation of the polymerase, the sample 50 may be held for about 2 minutes in the high temperature region 536 before starting the thermal cycle.

Described above is an explanation of the present invention based on the embodiments. These embodiments are intended to be illustrative only, and it will be obvious to those skilled in the art that various modifications to constituting elements and processes could be developed and that such modifications are also within the scope of the present invention.

Sequence Listing Free Text

Sequence number 1: Forward PCR Primer
Sequence number 2: Reverse PCR Primer
Sequence number 3: Probe

SEQUENCE LISTING

NSG-70055WOsequencelisting.txt

What is claimed is:

1. A reaction processor for applying thermal cycle to a liquid sample to cause a reaction to the sample, the reaction processor comprising:

a reaction processing vessel having for the sample to move therein, a pair of air communication ports provided at respective ends of the channel, the reaction processing vessel being detachable from the reaction processor;

a temperature control system including a heater for heating a part of the channel, the temperature control system configured to provide a first temperature region maintained at a first temperature and a second temperature region maintained at a second temperature higher than the first temperature between the pair of air communication port in the channel; and a liquid feeding system communicating with the channel via one of the pair of air communication ports, the liquid feeding system discharging and sucking air in order to move the sample in a reciprocating manner inside the channel, wherein the pair of air communication ports includes a first air communication port far from the second temperature region and a second air communication port close to the second temperature region, wherein the liquid feeding system includes:

a chamber having an internal space with a constant volume, a first air vent and a second air vent allowing the internal space to communicate with the outside of the chamber;

a first pump consisting of a first micro blower with a first discharging port connected to the first vent of the chamber, the first pump installed in the internal space of the chamber; and a second pump consisting of a second micro blower with a second discharging port connected to the second vent of the chamber, the second pump installed in the internal space of the chamber, wherein the first air vent of the chamber communicates via a tube with the first air communication port, wherein the second air vent of the chamber is opened to atmospheric pressure, wherein the second air communication port is opened to atmospheric pressure, wherein the liquid feeding system is controlled to operate the first pump and stop the second pump, the chamber sucks air from the second vent through the second pump and discharges air into the channel through the first communication port, the sample is controlled to move from the first temperature region to the second temperature region, and wherein the liquid feeding system is controlled to operate the second pump and stop the first pump, the chamber discharges air from the second vent of the chamber and sucks air from the channel through the first communication port, the sample is controlled to move from the second temperature region to the first temperature region.

2. The reaction processor according to claim 1, wherein the reaction processing vessel have a filter to prevent a contamination into the channel between the first air communication port and the first temperature region.

3. The reaction processor according to claim 1, the reaction processing vessel having a connection channel between the first temperature region and the second temperature region, further comprising:

a fluorescence detector that detects fluorescence from the sample inside the connection channel.

4. The reaction processor according to claim 3, wherein the liquid feeding system is controlled based on a change in the fluorescence detected by the fluorescence detector.

* * * * *